United States Patent [19]
Turner et al.

[11] Patent Number: 5,326,558
[45] Date of Patent: Jul. 5, 1994

[54] MEGAKARYOCYTOPOIETIC FACTOR

[75] Inventors: Katherine Turner, Melrose; Steven C. Clark, Winchester; Thomas G. Gesner, Beverly; Rodney M. Hewick, Lexington, all of Mass.

[73] Assignee: Genetics Institute, Inc., Cambridge, Mass.

[21] Appl. No.: 546,114

[22] Filed: Jun. 29, 1990

Related U.S. Application Data

[63] Continuation-in-part of Ser. No. 457,196, Dec. 28, 1989, abandoned, which is a continuation-in-part of Ser. No. 390,901, Aug. 8, 1989, abandoned.

[51] Int. Cl.$^5$ .................... C07K 15/00; A61K 37/02
[52] U.S. Cl. ................... 424/85.1; 530/351; 530/350; 530/820; 530/827; 930/145; 930/140
[58] Field of Search ............... 530/351, 395, 820, 827; 435/69.5, 69.6; 424/85.1

[56] References Cited

U.S. PATENT DOCUMENTS

| | | | |
|---|---|---|---|
| 4,658,018 | 4/1987 | Urdal et al. | 530/350 |
| 4,894,440 | 1/1990 | Rosenberg | 530/350 |

FOREIGN PATENT DOCUMENTS

| | | |
|---|---|---|
| 598297B2 | 6/1990 | Australia . |
| 354989 | 2/1990 | European Pat. Off. . |
| 89111714.5 | 2/1990 | European Pat. Off. . |
| WO9003397 | 4/1990 | PCT Int'l Appl. . |

OTHER PUBLICATIONS

Hoffman et al, *Blood Cells* 13, 1987, pp. 75–86.
DeAlarcon, *Blood Cells* 15, 1989, pp. 173–185.
Boznara et al, *Exp Hematol* 15, 1987, pp. 679–684.
Langley et al, *Exp Hematol* vol. 18, 1990, p. 615 (abstr art only).
Colony Stimulating Factors, 1990, ed Dexter, pp. 215–229.
Megakaryocyte Biology and Precursors, ed Evalt et al, 1981, pp. 59–75.
Hoffman, *Blood* 74:1196–1212 (1989).
Greenberg, *J. of Biol. Chem.* 262:3269–3277 (1987).
R. Hoffman et al, *J. Clin. Invest.*, 75:1174–1182 (1985).
H. H. Yang et al, *Chem. Abstr.*, 105(5):36292x (1986).
M. Kawakita et al, *Chem. Abstr.*, 105(13):109405y (1986).
T. Miyake et al, *Chem. Abstr.*, 98(11):83667v (1982).
M. Kawakita et al, *Prog. Clin. Biol. Res.*, 215:201–208 (1986).

*Primary Examiner*—Garnette D. Draper
*Attorney, Agent, or Firm*—Maureen C. Meinert; Thomas J. DesRosier

[57] ABSTRACT

A novel human megakaryocytopoietic factor capable of stimulating the growth and development of colonies of megakaryocytes is provided, including procedures for its purification and use as a pharmaceutical agent.

7 Claims, 7 Drawing Sheets

FIGURE 1

Partial Clone Containing Exon I

```
TTTCATAAGC ATTAGTGATA ATGTATGACT CAGCACCTGG CATAGAGAAG    50

CTCAATAAAT GGCAACTGCT AATCATCAAA ACCACAGATC GGTAGTAGCT   100

GTAGCTGCCA CCTCTTCCTT AGGAGTATCA CCCTCTTTAG GCAAAGCCAT   150

TACTTTGCCT GGTTTTCAAA AATGTGTTTA TCATCTCAGT CTAGTGAAGA   200

ATAAAGTGAC ATAATTGAGA TCACCTAAGA CATCAGCCAA ATATCAGCTG   250

GGCCTATTGC TGACATCATT CCAACACCTT CTCGATCAAT AA AAT TCT   298
                                                Asn Ser
```

```
CTC TCA CCA AGT GGC TTT GTC CCC CTC GTT AGA TTG CTC CCT  340
Leu Ser Pro Ser Gly Phe Val Pro Leu Val Arg Leu Leu Pro

TTC TAT AAA GTG GTT TGG CCA TAT TTA CGC CAG TAT TGT ATA  382
Phe Tyr Lys Val Val Trp Pro Tyr Leu Arg Gln Tyr Cys Ile

ATT TTA GAT TTA TCA AGC TGT GCA GGG AGA TGT GGG GAA GGG  424
Ile Leu Asp Leu Ser Ser Cys Ala Gly Arg Cys Gly Glu Gly

TAT TCT AGA GAT GCC ACC TGC AAC TGT GAT TAT AAC TGT CAA  466
Tyr Ser Arg Asp Ala Thr Cys Asn Cys Asp Tyr Asn Cys Gln

CAC TAC ATG GAG TGC TGC CCT GAT TTC AAG AGA GTC TGC ACT  508
His Tyr Met Glu Cys Cys Pro Asp Phe Lys Arg Val Cys Thr

GCG GGTAAGTCCT GAGAGCGGGT GTCTCCTCTG TCAAGCAACA          551
Ala

CTGCGAGTCT GTGAGTCCCC CCTTGCACCC TCGTGCAATG CTGTGAGACT   601

GAGCCTCCCC TTGCACCCAC TT                                 623
```

FIGURE 1A

Partial Clone Containing Exon II

```
TCTAGAGGAT CTGTACATTC AATTACTGTG AATCTATTAC AAAGCAGTGT   50

GTGAAGAGGA GAAGGATGAA GAGATTTCAT ATGAAGGCTA TCTCACTATC   100

TAGACATTTC CCGATTTTTC TTTGTCCATA CATGTAAATA ACTCGGGCAG   150

CATCAGGATG TCTCTTGGAG TCTGGAAGGG CAAGAGGAGT TGCCCTCAGT   200

CACCATATTT CTTTTTTGAC TTGGGCTGTC TCCATCTGGG ATACCATCTA   250

ATTTTTCCTG GATGATGTAC TCCAAATTTC AAATAAAAGA CTTAGAAATG   300

AACTTTTGGA AACCTAGTCA AGTCTAAGGT GGGAAATGGC TGTCAAATAC   350

GTGGGCCTGG CTTCACAATG AATAATCTGT AACTTCTTGT TTTGCTCTGG   400
```

```
GTA GAG CTT TCC TGT AAA GGC CGC TGC TTT GAG TCC TTC GAG   442
    Glu Leu Ser Cys Lys Gly Arg Cys Phe Glu Ser Phe Glu

AGA GGG AGG GAG TGT GAC TGC GAC GCC CAA TGT AAG AAG TAT   484
Arg Gly Arg Glu Cys Asp Cys Asp Ala Gln Cys Lys Lys Tyr

GAC AAG TGC TGT CCC GAT TAT GAG AGT TTC TGT GCA GAA       523
Asp Lys Cys Cys Pro Asp Tyr Glu Ser Phe Cys Ala Glu
```

```
GGTAAGCATC ACAGTACCAA CCAATGCTTC TCAGTACAGC CAGATCCCCG   573

GGCGAGCTC                                                 592
```

FIGURE 1B

Partial Clone Containing Exon III

```
TTTTATAGCA ATGCATCCTT AGCTTAAATG GAGTATTCGT GTTGAGCTGG    50

AGCCTGCCTG CACTGGCTGT CACCAGCATC TACTCTTGAA GCTAGATGCA   100

TCTGTGCTTT TCACAGTTAG AGCTGCTGAT GAACATAAAC AAGATGTTAA   150

CTGACTTGTC TTACTTGGCC TCA GTG CAT AAT CCC ACA TCA CCA   194
                         Val His Asn Pro Thr Ser Pro

CCA TCT TCA AAG AAA GCA CCT CCA CCT TCA GGA GCA TCT CAA 236
Pro Ser Ser Lys Lys Ala Pro Pro Pro Ser Gly Ala Ser Gln

ACC ATC AAA TCA ACA ACC AAA CGT TCA CCC AAA CCA CCA AAC 278
Thr Ile Lys Ser Thr Thr Lys Arg Ser Pro Lys Pro Pro Asn

AAG AAG AAG ACT AAG AAA GTT ATA GAA TCA GAG GAA ATA ACA 320
Lys Lys Lys Thr Lys Lys Val Ile Glu Ser Glu Glu Ile Thr

GAA GGT AGG AAG ATG ACA GAT ATA ATC AAA GGA GCT TTC TTA 362
Glu Gly Arg Lys Met Thr Asp Ile Ile Lys Gly Ala Phe Lys

GAT GAA GTA ACT TGT AGG TGACTGCTTA TCTAAGCCCA TTCTCAGAGA 410
Asp Glu Val Thr Cys Arg

ACAGGGTAAT CTTAGGAATC ATGAGCCTCA TTACACTCGA AGGTTTTAGA   460

CTTTGCTTTT AAGTAAAGTT TAAGACAAAG TATAAACTCT CAGCTCTTTC   510

TGTATTTACC AAACCCAGCA TGAGTCTGGG TTAAAACAAA TCAGAAGGGA   560

CAAATCTTAC TATAAAAAAC AAAAACCACC CCATGATTTT CTTTGTAGAA   610

TAATTTGATT CTGTGTTTTG GAGGATATGG GAAAGTTGAG AGATACTAGT   660
```

FIGURE 1C

AATACTGCTA GTATCTGTGA TAAGCCCAGG TGCCTTGCTT TTAACTGACA  710

GATTAAAAGG CAGTTGGTCA TATTACTAAT AAAAGCAAAA TCCAGATACT  760

TGTAGACTAG TAAATAGCAC TTCTTGCTGT GTTTAGACTG GTGGTTCTTT  810

TTTGTTTTAA ATCACAGTTG GTGTGATCC  839

FIGURE 2

Putative Partial cDNA of Meg-CSF (1)
AAT TCT CTC TCA CCA AGT GGC TTT GTC CCC CTC GTT AGA TTG
Asn Ser Leu Ser Pro Ser Gly Phe Val Pro Leu Val Arg Leu

(20)
CTC CCT TTC TAT AAA GTG GTT TGG CCA TAT TTA CGC CAG TAT
Leu Pro Phe Tyr Lys Val Val Trp Pro Tyr Leu Arg Gln Tyr

(30)          (40)
TGT ATA ATT TTA GAT TTA TCA AGC TGT GCA GGG AGA TGT GGG
Cys Ile Ile Leu Asp Leu Ser Ser Cys Ala Gly Arg Cys Gly

(50)
GAA GGG TAT TCT AGA GAT GCC ACC TGC AAC TGT GAT TAT AAC
Glu Gly Tyr Ser Arg Asp Ala Thr Cys Asn Cys Asp Tyr Asn

(60)          (70)
TGT CAA CAC TAC ATG GAG TGC TGC CCT GAT TTC AAG AGA GTC
Cys Gln His Tyr Met Glu Cys Cys Pro Asp Phe Lys Arg Val

(80)
TGC ACT GCG GAG CTT TCC TGT AAA GGC CGC TGC TTT GAG TCC
Cys Thr Ala Glu Leu Ser Cys Lys Gly Arg Cys Phe Glu Ser

(90)
TTC GAG AGA GGG AGG GAG TGT GAC TGC GAC GCC CAA TGT AAG
Phe Glu Arg Gly Arg Glu Cys Asp Cys Asp Ala Gln Cys Lys (100)         (110)
AAG TAT GAC AAG TGC TGT CCC GAT TAT GAG AGT TTC TGT GCA
Lys Tyr Asp Lys Cys Cys Pro Asp Tyr Glu Ser Phe Cys Ala (120)
GAA GTG CAT AAT CCC ACA TCA CCA CCA TCT TCA AAG AAA GCA
Glu Val His Asn Pro Thr Ser Pro Pro Ser Ser Lys Lys Ala (130)         (140)
CCT CCA CCT TCA GGA GCA TCT CAA ACC ATC AAA TCA ACA ACC
Pro Pro Pro Ser Gly Ala Ser Gln Thr Ile Lys Ser Thr Thr (150)
AAA CGT TCA CCC AAA CCA CCA AAC AAG AAG AAG ACT AAG AAA
Lys Arg Ser Pro Lys Pro Pro Asn Lys Lys Lys Thr Lys Lys

FIGURE 2A

```
                        (160)
GTT ATA GAA TCA GAG GAA ATA ACA GAA GGT AGG AAG ATG ACA
Val Ile Glu Ser Glu Glu Ile Thr Glu Gly Arg Lys Met Thr (170)                                  (180)
GAT ATA ATC AAA GGA GCT TTC TTA GAT GAA GTA ACT TGT AGG
Asp Ile Ile Lys Gly Ala Phe Lys Asp Glu Val Thr Cys Arg
```

A Restriction Map of Meg-CSF Genomic Clone

MEGAKARYOCYTOPOIETIC FACTOR

This application is a continuation-in-part of application Ser. No. 07/457,196, filed Dec. 28, 1989 (now abandoned), which is a continuation-in-part of application Ser. No. 07/390,901, filed Aug. 8, 1989 (now abandoned).

The present invention relates generally to a novel protein factor which is important in regulating the human hematopoietic system. More specifically the invention discloses a novel protein factor that stimulates megakaryocytic colony formation and the differentiation or maturation of megakaryocyte progenitors. Also provided are processes for obtaining the factor in homogeneous form and producing it by recombinant genetic engineering techniques.

BACKGROUND OF THE INVENTION

Megakaryocytes are the hematopoietic cells, largely found in the bone marrow, but also in peripheral blood and perhaps other tissues as well, which produce platelets (also known as thrombocytes) and subsequently release them into circulation. Megakaryocytes, like all of the hematopoietic cells of the human hematopoietic system, ultimately derive from a primitive stem cell after passing through a complex pathway comprising many cellular divisions and considerable differentiation and maturation.

The platelets derived from these megakaryocytic cells are critical for initiating blood clot formation at the site of injury. Platelets also release growth factors at the site of clot formation that speed the process of wound healing and may serve other functions. However, in patients suffering from depressed levels of platelets (thrombocytopenia) the inability to form clots is the most immediate and serious consequence, a potentially fatal complication of many therapies for cancer. Such cancer patients are generally treated for this problem with platelet transfusions. Other patients frequently requiring platelet transfusions are those undergoing bone marrow transplantation or patients with aplastic anemia.

Platelets for such procedures are obtained by plateletpheresis from normal donors. Like most human blood products, platelets for transfusion have a relatively short shelf-life and also expose the patients to considerable risk of exposure to dangerous viruses, such as the human immunodeficiency virus (HIV).

Clearly the ability to stimulate endogenous platelet formation in thrombocytopenic patients with a concomitant reduction in their dependence on platelet transfusion would be of great benefit. In addition the ability to correct or prevent thrombocytopenia in patients undergoing radiation therapy or chemotherapy for cancer would make such treatments safer and possibly permit increases in the intensity of the therapy thereby yielding greater anti-cancer effects.

For these reasons considerable research has been devoted to the identification and purification of factors involved in the regulation of megakaryocyte and platelet production. Although there is considerable controversy, the factors regulating the growth and differentiation of hematopoietic cells into mature megakaryocytes and the subsequent production of platelets by these cells are believed to fall into two classes: (1) megakaryocyte colony-stimulating factors (meg-CSFs) which support the proliferation and differentiation of megakaryocytic progenitors in culture, and (2) thrombopoietic (TPO) factors which support the differentiation and maturation of megakaryocytes resulting in the production and release of platelets. [See, e.g., E. Mazur, *Exp. Hematol.*, 15:340–350 (1987).]

Either class of factors is defined by bioassay. Factors with meg-CSF activity support megakaryocyte colony formation, while factors with TPO activity elicit an elevation in the numbers of circulating platelets when administered to animals. It is not clear how many species of factors exist that have either or both of these activities. For example, human IL-3 supports human megakaryocyte colony formation and, at least in monkeys, also frequently elicits an elevation in platelet count. However, IL-3 influences hematopoietic cell development in all of the hematopoietic lineages and can be distinguished from specific regulators of megakaryocytopoiesis and platelet formation which interact selectively with-cells of the megakaryocytic lineage.

From the studies reported to date, it is not clear whether activities identified as meg-CSF also have TPO activity or vice versa. Many different reports in the literature describe factors which interact with cells of the megakaryocytic lineage. Several putative meg-CSF compositions have been derived from serum [See, e.g., R. Hoffman et al, *J. Clin. Invest.*, 75:1174–1182 (1985); J. E. Straneva et al, *Exp. Hematol.*, 15:657–663 (1987); E. Mazur et al, *Exp. Hematol.*, 13:1164–1172 (1985]. A larger number of reports of a TPO factor are in the art. [See, e.g., T. P. McDonald, *Exp. Hematol.*, 16:201–205 (1988); T. P. McDonald et al, *Biochem. Med. Metab. Biol.*, 37:335–343 (1987); T. Tayrien et al, *J. Biol. Chem.*, 262:3262–3268 (1987) and others].

Although there have been numerous additional reports tentatively identifying such regulatory factors, the biochemical and biological identification and characterization of these factors has been hampered by the small quantities of the naturally occurring factors available from natural sources, e.g., blood and urine. At present there is no identification of a single purified factor useful as a meg-CSF or TPO for pharmaceutical use in replacing serum-derived products or platelets.

There remains a need in the art for additional proteins purified from their natural sources or otherwise produced in homogeneous form, which are capable of stimulating or enhancing the production of platelets in vivo, to replace presently employed platelet transfusions.

BRIEF SUMMARY OF THE INVENTION

In one aspect the present invention provides a novel human megakaryocytopoietic factor (meg-CSF) which is substantially free from other human proteins. This protein may be produced by recombinant genetic engineering techniques. It may also be purified from cell sources producing the factor naturally or upon induction with other factors. meg-CSF may also be synthesized by chemical techniques, or a combination of the above-listed techniques.

The meg-CSF of the present invention has been found to stimulate the growth and development of colonies consisting of intermediate and large size megakaryocytes in an assay using murine bone marrow target cells. meg-CSF displays biological activity in this assay of greater than $5 \times 10^7$ dilution units per milligram of protein. meg-CSF has also displayed activity in an assay using human cells, as described in Example 8 below.

Active meg-CSF has an apparent molecular weight of approximately 28-38 kd as determined by sodium dodecyl sulfate polyacrylamide gel electrophoresis under non-reducing conditions. meg-CSF has an apparent molecular weight of approximately 20-27 kd as determined by sodium dodecyl sulfate polyacrylamide gel electrophoresis under reducing conditions.

The active approximately 28-38 kd meg-CSF is further characterized by comprising all or a portion of the sequence of FIG. 1 or 2. Meg-CSF is also characterized by comprising at least one of the same or substantially the same four amino acid sequences or fragments thereof, recited below as sequences (a) through (d).

Another aspect of the present invention is a DNA sequence that encodes the expression of a human meg-CSF protein. This DNA sequence may include an isolated DNA sequence that encodes the expression of a human meg-CSF protein as described above. The DNA sequence coding for all or a portion of the meg-CSF protein is characterized as comprising the same or substantially the same nucleotide sequence in FIG. 1 or 2 or fragments thereof. This DNA sequence may include additional coding sequence. The DNA sequence may also include 5' and 3' human non-coding sequences flanking the meg-CSF coding sequence. The DNA sequence may also encode an amino terminal signal peptide. FIG. 1 illustrates three exons forming a partial genomic coding sequence of human meg-CSF isolated from human urine and expressed in COS-1 cells. FIG. 2 illustrates a putative partial cDNA coding sequence derived from the genomic sequence.

It is understood that the DNA sequence of this invention may encodes a biologically active human meg-CSF protein and may also comprise DNA sequences capable of hybridizing under appropriate conditions, or which would be capable of hybridizing under said conditions, but for the degeneracy of the genetic code, to an isolated DNA sequence of FIG. 1 or 2. Thus, the DNA sequence of this invention may include or contain modifications in the non-coding sequences, signal sequences or coding sequences based on allelic variation, species variation or deliberate modification.

Still a further aspect of the present invention is a process for isolating and purifying the meg-CSF composition of the present invention or a fragment thereof from human urine. This purification process provided by the present invention involves the steps of concentrating the urine; subjecting it to anion exchange column chromatography; followed by cation exchange column chromatography; subjecting the resulting materials to lectin affinity chromatography followed by cation exchange fine performance liquid chromatography (FPLC) and three elutions through reverse phase high pressure liquid chromatography (HPLC) using different solvent solutions for each HPLC run.

A further aspect of the present invention is homogeneous meg-CSF, purified from urine or produced via recombinant or synthetic techniques, which is characterized by a specific activity in the murine fibrin clot assay of greater than $5 \times 10^7$ dilution units/mg.

Also provided by the present invention is a recombinant DNA molecule comprising vector DNA and an DNA sequence encoding human meg-CSF. The DNA molecule provides the meg-CSF DNA in operative association with a regulatory sequence capable of directing the replication and expression of meg-CSF in a selected host cell. Host cells transformed with such DNA molecules for use in expressing recombinant meg-CSF protein are also provided by the present invention.

The DNA molecules and transformed cells of the invention are employed in another aspect, a novel process for producing recombinant human meg-CSF protein, or peptide fragments thereof. In this process a cell line transformed with a DNA sequence encoding expression of meg-CSF protein or a fragment thereof (or a recombinant DNA molecule as described above) in operative association with a suitable regulatory or expression control sequence capable of controlling expression of the protein is cultured under appropriate conditions permitting expression of the recombinant DNA. The expressed meg-CSF protein is then harvested from the host cell, cell lysate or culture medium by suitable conventional means. The conditioned medium may be processed through the same purification steps or modifications thereof as used to isolate the meg-CSF from urine. This claimed process may employ a number of known cells as host cells for expression of the protein. Presently preferred cell lines for producing meg-CSF are mammalian cell lines and bacterial cells.

As still a further aspect of the present invention, there is provided recombinant meg-CSF protein. This protein is substantially free from other human proteinaceous materials and comprising a DNA sequence encoding one or more of the peptide fragments or sequences described herein. The meg-CSF protein of this invention is also characterized by containing one or more of the physical, biochemical, pharmacological or biological activities described herein.

Another aspect of this invention provides pharmaceutical compositions containing a therapeutically effective amount of homogeneous or recombinant meg-CSF or an effective amount of one or more active peptide fragments thereof. These pharmaceutical compositions may be employed in methods for treating disease states or disorders characterized by a deficiency of platelets. Thus the meg-CSF composition of the present invention or pharmaceutically effective fragments thereof may be employed in the treatment of aplastic anemias resulting from chemotherapy or thrombocytopenia. Meg-CSF may be used as an adjunctive therapy for bone marrow transplant patients.

A further aspect of the invention, therefore, is a method for treating these and other pathological states resulting from a deficiency of platelets by administering to a patient a therapeutically effective amount of meg-CSF or one or more peptide fragments thereof in a suitable pharmaceutical carrier. These therapeutic methods may include administering simultaneously or sequentially with meg-CSF or one or more peptide fragments thereof an effective amount of at least one other TPO-like factor, a cytokine, hematopoietin, interleukin, growth factor, or antibody.

Still another aspect of the present invention are antibodies directed against human meg-CSF or a fragment thereof. As part of this aspect, therefore, the invention claims cell lines capable of secreting such antibodies and methods for their production and use in diagnostic or therapeutic procedures.

Other aspects and advantages of the present invention will be apparent upon consideration of the following detailed description of preferred embodiments thereof.

BRIEF DESCRIPTION OF THE DRAWINGS

FIGS. 1, 1A-1C illustrate the subcloned partial genomic DNA sequence obtained in accordance with Example 5.

FIGS. 2 and 2A illustrate the putative cDNA and amino acid sequence of the meg-CSF of the present invention.

DETAILED DESCRIPTION OF THE INVENTION

Figure 3:
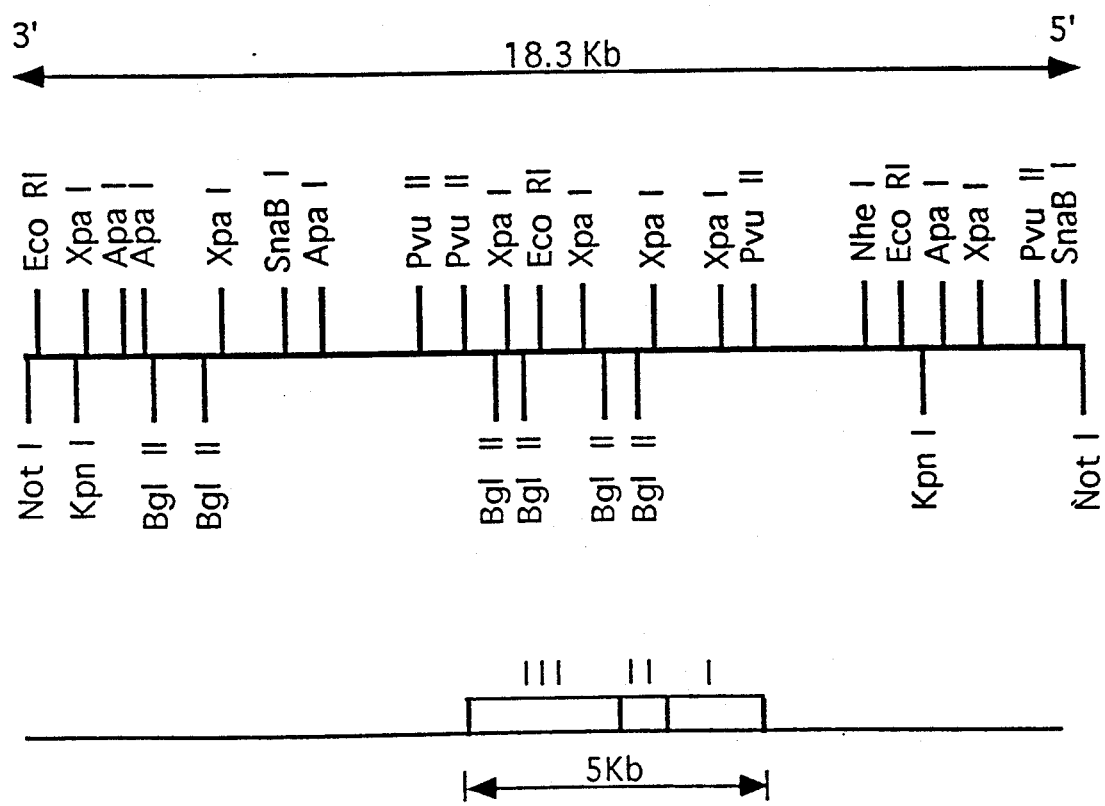
FIG. 3 illustrates a restriction map illustrating the position of restriction endonuclease enzymes of the 18.3 kb genomic clone, as well as the positions of each of the three exons of FIG. 1.

The novel human megakaryocyte colony stimulating factor, meg-CSF, provided by the present invention is a homogeneous protein or proteinaceous composition substantially free of association with other human proteinaceous materials. This protein can be produced via recombinant techniques to enable large quantity production of pure, active meg-CSF useful for therapeutic applications. Alternatively this protein may be obtained as a homogeneous protein purified from human urine or a mammalian cell line secreting or expressing it. Further meg-CSF or active fragments thereof may be chemically synthesized.

Meg-CSF of the present invention is characterized by one or more of the following biochemical and biological properties:

(1) The composition of the present invention has an apparent molecular weight of approximately 28-38 kd as determined by 12% sodium dodecyl sulfate polyacrylamide gel electrophoresis (SDS-PAGE) under non-reducing conditions and by murine fibrin clot megakaryocyte colony formation bioassay;

(2) The composition of the present invention has an apparent molecular weight of approximately 20-27 kd as determined by 12% SDS-PAGE under reducing conditions using a variety of reducing agents, e.g., beta-mercaptoethanol or dithiothreitol;

(3) The composition of the present invention has a specific activity in the murine fibrin clot megakaryocyte colony formation assay of greater than approximately $5 \times 10^7$ dilution units/mg protein.

(4) The meg-CSF composition of the present invention contains one or more of the same or substantially the same amino acid sequences or fragments thereof:

(a) Ser Arg Cys Phe Glu Ser Phe Glu Arg (b) Arg Val Cys Thr Ala Glu Leu Ser Cys Lys Gly (Arg)

(c) Lys Ala Pro Pro Pro (X) Gly Ala Ser Gln Thr Ile Lys (d) Lys Tyr Asp Lys Cys Cys Pro Asp Tyr Glu Ser Phe Cys Ala Glu Val His Asn Pro (e) an amino acid sequence of Table I or II below.

These sequences or fragments of these sequences may also have biological or physiological activity similar to that of the complete meg-CSF protein. In the sequences, (X) indicates that the residue is not yet absolutely identified, but may be Ser or Thr; and () indicates tentative identification of a residue. The sequences identified above as (a) through (d) were originally determined from purified material from step 8, the third HPLC purification step of the purification procedure, omitting step 7. The same sequences also have been obtained from the material, when purified through all eight steps detailed below. The sequences of FIG. 1 were obtained from partial genomic clones of human meg-CSF and contain exon I, II and III obtained as described below. The sequence of FIG. 2 is a putative partial cDNA sequence of human meg-CSF in which the three exons are contained within a single reading frame. The 5' and 3' borders of this cDNA are undetermined, indicating that the N-terminal Met-containing exon is presently unidentified.

(5) The meg-CSF composition of the present invention is capable of binding SP-Zeta Prep under acidic conditions of pH4.5.

(6) The meg-CSF composition of the present invention is capable of binding to Wheat Germ-Sepharose and Concanavalin-A Sepharose.

(7) The meg-CSF composition of the present invention elutes between 23-33% acetonitrile on a reverse-phase C4 HPLC column using a solvent system of trifluoroacetic acid (TFA) and acetonitrile.

(8) The meg-CSF composition of the present invention elutes between 6-15% n-propanol on a reverse-phase C18 HPLC column using a solvent system of pyridine, acetic acid and n-propanol.

(9) The meg-CSF composition of the present invention elutes between 27-37% acetonitrile on a reverse-phase C4 HPLC column using a solvent system of heptafluorobutyric acid (HFBA) and acetonitrile.

The biological activity of the meg-CSF composition of the present invention is demonstrated by its ability to stimulate the growth and development of colonies consisting of intermediate and large size megakaryocytes in culture. In the murine fibrin clot megakaryocyte colony formation assay, the meg-CSF composition of the present invention stimulates colonies of an average of 3-6 megakaryocytes. In the murine agar meg-CSF assay, the meg-CSF composition of the present invention stimulates colonies of megakaryocytes. The meg-CSF composition of the present invention has inconsistently shown activity in the human plasma clot megakaryocyte colony formation assay.

meg-CSF was originally detected in the urine of human patients with bone marrow transplants. These patients demonstrate an enhanced level of meg-CSF activity. Human meg-CSF was initially purified from this human urine by a sequence of purification steps and techniques specifically described in Example 1 below. However, this factor may also be purified from other sources, e.g., human cell lines, or produced via recombinant means from those cell lines.

The purification techniques employed in obtaining meg-CSF from the human urine comprises the following steps. The purification steps include concentrating pooled bone marrow transplant patient urine through an Amicon YM-10 filter. The concentrated urine is passed through an anion exchange chromatographic column and the flow-through is bound onto a cation exchange chromatographic column. The urinary protein eluate was then subjected to pooling, dialyzing and heating and applying it to a lectin affinity chromatographic column. This eluate is then dialyzed and applied to a cation exchange FPLC column. Finally this eluate is applied through three cycles of reverse phase HPLC using different solvent systems.

Batches with the highest levels of meg-CSF in the murine fibrin clot assay, described below, were selected for further purification at the semi-preparative scale (between 30 and 100 liters urine equivalent) to maximize recovery and yield.

Thus the homogeneous meg-CSF may be obtained by applying the above purification procedures, which are described in detail in Example 1, to human urine or other sources of human meg-CSF, e.g., activated peripheral blood leukocytes and human placenta. Other tissue sources and cell lines such as C10-MJ2 (an HTLV1-transformed T cell line) and HEK (primary human embryonic kidney cells) may also be sources of this protein. Procedures for culturing a cell source which may be found to produce meg-CSF are known to those of skill in the art.

Meg-CSF or one or more peptide fragments thereof may also be produced via recombinant techniques. To obtain the genomic DNA and cDNA sequences for meg-CSF or one or more fragments thereof, tryptic digests of the purified, sequenced polypeptide were prepared, i.e. the tryptics identified as (a) through (d) above, by conventional techniques.

As described in detail in Example 5, below oligonucleotide probes were synthesized using the genetic code to predict all possible sequences that encode the amino acid sequences of the tryptic fragments or the above-identified amino terminal sequence of meg-CSF. The probes were employed to screen a human placenta lambda phage DNA library (a human genomic library). One of the probes hybridized to an 18.3 kb genomic DNA insert. A restriction map of this insert is illustrated in FIG. 3. The region hybridizing to the probe was subcloned, sequenced and is illustrated in FIG. 1, with the open reading frame labeled Exon II. The 18.3 kb genomic DNA fragment also hybridized to two additional probes. The hybridizing regions were individually subcloned, sequenced and shown to contain the sequences illustrated in FIG. 1 as Exons I and III within open reading frames. All four tryptic sequences are present in the three exons.

Two of the tryptics overlapped intron/exon junctions and define the borders of Exon II. The 5' border of Exon I and the 3' border of Exon III are undetermined. It is presently speculated that a possible site for the 5' border of Exon I (i.e., where the N-terminal Met-containing exon or the 5'-adjacent exon would splice) is after nucleotide #391 in FIG. 1, Exon I.

The putative cDNA sequence and predicted amino acid sequence (three letter code) of three exons containing the meg-CSF partial cDNA sequence are reported in FIG. 2 below. The partial sequence contains 182 amino acids and 546 nucleotides, containing all four of the tryptic sequences above.

The nucleotide sequence of this meg-CSF sequence, specifically Exon I and Exon II, has been compared with the nucleotide sequences recorded in protein and DNA databanks. The amino terminus of vitronectin, the serum adhesion molecule, was observed to have the highest degree of sequence similarity. The amino terminal portion is also called Somatomedin B, a peptide found in the circulation. Other significant sequence similarities were found at the protein and DNA levels to the B domain of von Willebrand factor, made by endothelial cells and megakaryocytes and at the protein level in the extracellular domain of murine PC-1, a membrane glycoprotein dimer found on IgG secreting plasma cells. These peptides are functionally unrelated, with Somatomedin B and PC-1 having unknown functions.

To obtain the entire genomic and cDNA sequences the amino and carboxy terminii of meg-CSF may be determined by various procedures. One procedure involves the preparation of a cDNA library from activated human peripheral blood leucocytes or other sources of meg-CSF RNA and extraction of the full length cDNA by hybridization, using the three known exons as probes. A second method is expression cloning in COS cells. For example, different sections of the 18.3 kb genomic insert are subcloned into COS cells and different activities identified. If a protein is located, the RNA of that clone is isolated and cDNA prepared therefrom and expressed to obtain the protein. For example, this method involves subcloning either the full length human genomic clone, or different sections of the 18.3 kb genomic insert into an expression vector, transfecting into COS cells, preparing a cDNA library from meg-CSF transfected COS cells and screening by hybridization for meg-CSF cDNA. Alternatively, the entire sequence, including the N-terminal Met, may be identified by comparison with the murine homolog of meg-CSF. Also, the mRNA from a cell source of meg-CSF can be used to make a cDNA library which can be screened with the probes to identify the cDNAs encoding the meg-CSF polypeptide. Presently employed techniques to screen for cDNA sources include making primers from Exons I-III and employing PCR techniques to isolate and amplify cDNA transcripts.

The full-length human genomic clone or fragments thereof may also be employed as probes to isolate by cross-hybridization the murine genomic equivalent of meg-CSF. The murine genomic clone of meg-CSF or fragments thereof can be used to identify a mRNA source for meg-CSF which can be used to make a murine cDNA library. The murine cDNA can be used to identify the corresponding exons in the human meg-CSF gene which can then be spliced together to create a full length human cDNA.

Once the entire cDNA is identified, it or any portion of it that encodes an active fragment of meg-CSF, can be introduced into any one of a variety of expression vectors to make an expression system for meg-CSF or one or more fragments thereof.

By such use of recombinant techniques, DNA sequences encoding the meg-CSF polypeptide are obtained which contain DNA sequences encoding one or more of the tryptic fragments or the partial sequence identified above. The present invention also encompasses these DNA sequences, free of association with DNA sequences encoding other proteins, and coding on expression for meg-CSF polypeptides. These DNA sequences include those sequences encoding all or a fragment of the above-identified peptide sequences or partial clone sequence and those sequences which hybridize under stringent hybridization conditions [see, T. Maniatis et al, *Molecular Cloning (A Laboratory Manual)*, Cold Spring Harbor Laboratory (1982), pages 387 to 389]to the DNA sequences.

An example of one such stringent hybridization condition is hybridization in 4XSSC at 65° C., followed by a washing in 0.1XSSC at 65° C. for an hour. Alternatively an exemplary stringent hybridization condition is in 50% formamide, 4XSSC at 42° C.

DNA sequences which hybridize to the sequences for meg-CSF under relaxed hybridization conditions and which code on expression for meg-CSF peptides having meg-CSF biological properties also encode novel meg-CSF polypeptides. Examples of such non-stringent hybridization conditions are 4XSSC at 50° C. or hybridization with 30–40% formamide at 42° C. For example, a DNA sequence which shares regions of significant homology, e.g., sites of glycosylation or disulfide linkages, with the sequences of meg-CSF and encodes a protein having one or more meg-CSF biological properties clearly encodes a meg-CSF polypeptide even if such a DNA sequence would not stringently hybridize to the meg-CSF sequences.

Allelic variations (naturally-occurring base changes in the species population which may or may not result in an amino acid change) of DNA sequences encoding the peptide sequences of meg-CSF are also included in the present invention, as well as analogs or derivatives thereof. Similarly, DNA sequences which code for meg-CSF polypeptides but which differ in codon sequence due to the degeneracies of the genetic code or variations in the DNA sequence of meg-CSF which are caused by point mutations or by induced modifications to enhance the activity, half-life or production of the polypeptides encoded thereby are also encompassed in the invention.

meg-CSF polypeptides may also be produced by known conventional chemical synthesis. Methods for constructing the polypeptides of the present invention by synthetic means are known to those of skill in the art. The synthetically-constructed meg-CSF polypeptide sequences, by virtue of sharing primary, secondary, or tertiary structural and conformational characteristics with meg-CSF polypeptides may possess meg-CSF biological properties in common therewith. Thus, they may be employed as biologically active or immunological substitutes for natural, purified meg-CSF polypeptides in therapeutic and immunological processes.

Modifications in the peptides or DNA sequences encoding meg-CSF can be made by one skilled in the art using known techniques. Modifications of interest in the meg-CSF sequences may include the replacement, insertion or deletion of a selected amino acid residue in the coding sequences. Mutagenic techniques for such replacement, insertion or deletion are well known to one skilled in the art. [See, e.g., U.S. Pat. No. 4,518,584.]

Specific mutations of the sequences of the meg-CSF polypeptide may involve modifications of a glycosylation site. The absence of glycosylation or only partial glycosylation results from amino acid substitution or deletion at any asparagine-linked glycosylation recognition site or at any site of the molecule that is modified by addition of O-linked carbohydrate. An asparagine-linked glycosylation recognition site comprises a tripeptide sequence which is specifically recognized by appropriate cellular glycosylation enzymes. These tripeptide sequences are either Asp-X-Thr or Asp-X-Ser, where X can be any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

Other analogs and derivatives of the sequence of meg-CSF which would be expected to retain meg-CSF activity in whole or in part may also be easily made by one of skill in the art given the disclosures herein. One such modification may be the attachment of polyethylene glycol (PEG) onto existing lysine residues in the meg-CSF sequence or the insertion of one or more lysine residues or other amino acid residues that can react with PEG or PEG derivatives into the sequence by conventional techniques to enable the attachment of PEG moieties. Such modifications are believed to be encompassed by this invention.

The present invention also provides a method for producing meg-CSF polypeptides or active fragments thereof. One method of the present invention involves introducing the cDNA encoding a meg-CSF polypeptide into an expression vector to make an expression system for meg-CSF. A selected host cell is transformed with the vector and cultured. The method of this present invention therefore comprises culturing a suitable cell or cell line, which has been transformed with a DNA sequence coding on expression for a meg-CSF polypeptide under the control of known regulatory sequences. Regulatory sequences include promoter fragments, terminator fragments and other suitable sequences which direct the expression of the protein in an appropriate host cell. The expressed factor is then recovered, isolated and purified from the culture medium (or from the cell, if expressed intracellularly) by appropriate means known to one of skill in the art.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines, are the monkey COS-1 cell line, and the CV-1 cell line. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, MC1061 and strains used in the following examples) are well-known as host cells in the field of biotechnology. Various strains of *B. subtilis*, *Pseudomonas*, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

The present invention also provides recombinant molecules or vectors for use in the method of expression of novel meg-CSF polypeptides. These vectors contain the novel meg-CSF DNA sequences recited herein, and which alone or in combination with other sequences code for meg-CSF polypeptides of the invention or active fragments thereof. Alternatively, vectors incorporating modified sequences as described above are also embodiments of the present invention and useful in the production of meg-CSF polypeptides. The vector employed in the method also contains selected regulatory sequences in operative association with the DNA coding sequences of the invention and capable of directing the replication and expression thereof in selected host cells.

One desirable vector is pXM [Y. C. Yang et al, *Cell*, 47:3-10 (1986)]. Mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, *J. Mol. Biol.*, 159:511-521 (1982); and Kaufman, *Proc. Natl. Acad. Sci., USA*, 82:689-693 (1985). Alternatively, the vector DNA may include all or part of the bovine papilloma virus genome [Lusky et al, *Cell*, 36:391-401 (1984)] and be carried in cell lines such as C127 mouse cells as a stable episomal element. The transformation of these vectors into appropriate host cells can result in expression of the meg-CSF polypeptides.

Other appropriate expression vectors of which numerous types are known in the art for mammalian, insect, yeast, fungal and bacterial expression can also be used for this purpose.

Thus meg-CSF or active fragments thereof, purified to homogeneity from cell sources or produced recombinantly or synthetically, may be used in a pharmaceutical preparation or formulation to stimulate platelet recovery following chemotherapy or bone marrow transplantation, to treat thrombocytopenia, aplastic anemia and other platelet disorders. Therapeutic treatment of such platelet disorders or deficiencies with these meg-CSF polypeptide compositions may avoid undesirable side effects caused by treatment with presently available serum-derived factors or transfusions of human platelets. It may also be possible to employ one or more peptide fragments of meg-CSF, such as the peptides above-identified, in such pharmaceutical formulations.

The polypeptides of the present invention may also be employed, alone or in combination with other cytokines, hematopoietins, interleukins, growth factors or antibodies in the treatment of the above-identified conditions.

Therefore, as yet another aspect of the invention are therapeutic compositions for treating the conditions referred to above. Such compositions comprise a therapeutically effective amount of the meg-CSF protein or a therapeutically effective fragment thereof in admixture with a pharmaceutically acceptable carrier. This composition can be systematically administered parenterally. Alternatively, the composition may be administered intravenously. If desirable, the composition may be administered subcutaneously. When systematically administered, the therapeutic composition for use in this invention is in the form of a pyrogen-free, parenterally acceptable aqueous solution. The preparation of such pharmaceutically acceptable protein solutions, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 1-1000 micrograms of meg-CSF protein or fragment thereof or 50 to 5000 units (i.e., one unit being the minimum concentration of meg-CSF protein which yields the maximal number of colonies in the murine fibrin clot megakaryocyte colony formation assay) of protein per kilogram of body weight.

The therapeutic method, compositions and polypeptides of the present invention may also be employed, alone or in combination with other cytokines, hematopoietins, interleukins, growth factors or antibodies in the treatment of disease states characterized by other symptoms as well as platelet deficiencies. It is anticipated that this molecule, if it does not itself have TPO activity, will prove useful in treating some forms of thrombocytopenia in combination with general stimulators of hematopoiesis, such as IL-3, IL-6 or GM-CSF or with other megakaryocytic stimulatory factors or molecules with TPO-like activity. Additional exemplary cytokines or hematopoietins for such co-administration include TPO, G-CSF, CSF-1, GM-CSF, IL-1, IL-11 (described as IL-10 in co-owned copending U.S. patent application Ser. No. 07/441,100 now abandoned incorporated herein by reference), IL-3, IL-4, M-CSF, IL-7 or erythropoietin. The dosage recited above would be adjusted to compensate for such additional components in the therapeutic composition. Progress of the treated patient can be monitored by conventional methods.

Other uses for these novel polypeptides are in the development of antibodies generated by standard methods for in vivo or in vitro diagnostic or therapeutic use. Such antibodies may include both monoclonal and polyclonal antibodies, as well as chimeric antibodies or "recombinant" antibodies generated by known techniques. Also provided by this invention are the cell lines generated by presenting meg-CSF or a fragment thereof as an antigen to a selected mammal, followed by fusing cells of the animal with certain cancer cells to create immortalized cell lines by known techniques. The methods employed to generate such cell lines and antibodies directed against all or portions of a human meg-CSF polypeptide of the present invention are also encompassed by this invention.

The antibodies of the present invention may be utilized for in vivo and in vitro diagnostic purposes, such as by associating the antibodies with detectable labels or label systems. Alternatively these antibodies may be employed for in vivo and in vitro therapeutic purposes, such as by association with certain toxic or therapeutic compounds or moieties known to those of skill in this art. These antibodies also have utility as research reagents.

The following examples illustratively describe the purification and characteristics of homogeneous human meg-CSF and other methods and products of the present invention. These examples are for illustration and do not limit the scope of the present invention.

EXAMPLE 1

Purification of meg-CSF from Urine

The following procedures are presently employed to obtain homogeneous meg-CSF protein from urine of human bone marrow transplant patients. Urine from patients with aplastic anemia or thrombocytopenia accompanying other disease states may also be used as the source of the factor employing this purification.

STEP 1: Urine was collected from the bone marrow transplant patients between days 5 and 18 following transplant. One hundred liters of pooled urine were treated with protease inhibitors phenylmethylsulfonylfluoride (PMSF) and ethylenediaminetetraacetic acid (EDTA). This pooled urine was concentrated on an Amicon YM-10 filter (10,000 molecular weight cut-off) to remove excess pigments and reduce the volume. A cocktail of protease inhibitors (leupeptin, aprotinin, ethylene glycol-bis-tetraacetic acid (EGTA) and N-ethylmaleimide (NEM)) was added to the urine at this and the next three steps to minimize proteolysis. The pH of the urine concentrate was adjusted to 8.0 and diluted to a conductivity of 7mS/cm.

STEP 2: The retentate from this first step of the purification was then subjected to anion exchange column chromatography on a QAE Zetaprep [Cuno] at pH 8.0. The QAE flow-through was adjusted to a pH4.5 with 1M acetic acid.

STEP 3: The flow-through from the second purification step was bound to a cation exchange chromatographic column, an SP-Zetaprep column [Cuno] at pH 4.5. Bound protein containing meg-CSF was eluted with 1M NaCl at a pH of 4.5. The eluate was pooled, protease inhibitors were added as above and the materials stored at $-80°$ C. until further chromatography was performed. The eluate was then dialyzed against Tris-buffered saline (TBS), with the addition of the protease inhibitors described in Step 1. This dialyzate was heated at 56° C. for 30 minutes. Addition of the protease inhibitors, while not essential for recovery of protein, enabled greater amount of protein to be recovered from this step, undegraded by the proteases in the system. Pools from this step were also analyzed for the presence of megakaryocyte-specific growth factors. These pools were found to contain meg-CSF activity.

STEP 4: The resulting material was added to a lectin affinity chromatographic column, a Wheat Germ Sepharose column [Pharmacia] and eluted with 0.25M N-acetyl glucosamine (N-acglcNH$_2$) in TBS. Urinary meg-CSF was found to bind to this column. The bound protein was eluted from this column by 20 mM sodium acetate, pH 4.5 in the presence of the protease inhibitors of Step 1, which were added for the reasons described in Step 3.

STEP 5: This dialysate was applied to a 10 ml S-Toyopearl FPLC cation exchange column and eluted using a linear gradient of 0 to 1M NaCl in 20 mM sodium acetate at pH 4.5. The protein eluted from this step was tested for meg-CSF activity in the fibrin clot assay described below. The meg-CSF activity was observed to elute in two discrete peaks. The major activity eluted between 0.1M and 0.25M NaCl. A minor, but reproducible activity eluted between 0.3M and 0.5N NaCl. The two activities may be due to protein or carbohydrate modification of a single protein; however the data presented further herein refers to the major protein.

STEP 6: The eluate from this fifth purification step was then purified on a reverse phase HPLC (C4) column [Vydac; 1 cm×25 cm] which was eluted with a linear gradient of between 23–33% acetonitrile in 0.1% trifluoroacetic acid (TFA). This step removes an abundant 30 Kd protein contaminant.

STEP 7: The HPLC step was repeated in a different solvent system, after the eluate of Step 6 was diluted with two parts acetic acid and pyridine. The purified material eluted between 6–15% n-propanol in pyridine and acetic acid on a C18 reverse phase HPLC column (0.46×25 cm). The material produced after this step, when assayed gave the specific activity of greater than $5\times10^7$ dilution units reported in the murine assay. This optional step removes the bulk of urinary ribonuclease, a major contaminant, from the preparation.

STEP 8: The HPLC step was repeated once more on a C4 column (Vydac; 0.46×25 cm) using 0.15% HFBA in acetonitrile. The material eluted between 27–37% acetonitrile. The last HPLC step removed substantially all remaining ribonuclease and proteinaceous contaminants present after Step 7.

This purified meg-CSF material was then analyzed by SDS-PAGE, bioassayed and labelled with $^{125}$I. Homogenous protein is obtained from this procedure, omitting step 7, having a specific activity ranging from about $5\times10^7$ to about $2-5\times10^8$ dilution units per mg protein in the murine megakaryocyte colony assay described below.

EXAMPLE 2

Sodium Dodecyl Sulfate-Polyacrylamide Gel Electrophoresis

The purified protein was analyzed by SDS-PAGE performed according to the method of Laemmli [Laemmli, U. K., *Nature*, 227:680–685 (1970) ] on 12% acrylamide slab gels (0.75 mm thickness). After electrophoresis, the gels were either subjected to autoradiography to visualize $^{125}$I-labelled meg-CSF, or silver stain, or cut into 0.5–1 cm slices and eluted in 0.5 ml TBS with 0.3% deionized BSA overnight at 4° C. and assayed for meg-CSF activity. Apparent molecular weight was determined with protein standards: BRL prestained molecular weight markers, 14C molecular weight standards [NEN], or low molecular weight SDS-PAGE standards [Biorad].

A small aliquot of protein from Steps 6, 7 and 8 of Example 1 containing active meg-CSF was iodinated and subjected to SDS-PAGE. SDS-PAGE analysis (non-reducing conditions) of reverse phase purified meg-CSF from step 8 beginning with several fractions which eluted before the meg-CSF activity, continuing right through the active fractions and ending with fractions which eluted after the peak of meg-CSF activity, revealed the presence of one heterogenous protein band ranging in size between 28 and 38 kd. Elution of the protein from a parallel gel lane revealed that the bioactivity in the murine megakaryocyte colony formation assay correlated with the presence of the iodinated meg-CSF band in the gel.

Upon reduction, the majority of the protein has a molecular weight of between approximately 20–27 kd. Based on this information meg-CSF may be a dimer. The protein does not appear to be digestable with N-glycanase under standard conditions.

EXAMPLE 3

Recovery of Protein

Starting with 50 liters of urine, the final pooled active fractions from the HPLC column contained approximately 25 micrograms of protein, estimated from the amino acid composition of purified meg-CSF. The specific activity of the 28–38 kd meg-CSF protein was estimated to be greater than approximately $5\times10^7$ dilution units/mg in the murine fibrin clot assay described below. One unit of activity is defined as the reciprocal of the maximal dilution which stimulates maximal colony formation. One megakaryocyte colony is defined as 3 or more cells.

EXAMPLE 4 meg-CSF Protein Composition meg-CSF obtained from the eighth step of the purification of Example 1, omitting Step 7, was employed to obtain tryptic fragments for sequencing. Twenty-five micrograms of purified meg-CSF were desalted over a reverse phase column. The main peak was then fully reduced and alkylated, due to the large number of cysteines present therein. This material was again eluted through a reverse phase column, and the resulting material digested with trypsin (2% w/w). Sequencing provided the four peptide sequences:

(a) Ser Arg Cys Phe Glu Ser Phe Glu Arg
(b) Arg Val Cys Thr Ala Glu Leu Ser Cys Lys Gly (Arg)
(c) Lys Ala Pro Pro Pro (X) Gly Ala Ser Gln Thr Ile Lys
(d) Lys Tyr Asp Lys Cys Cys Pro Asp Thr Glu Ser Phe Cys Ala Glu Val His Asn Pro

X represents an ambiguously identified amino acid, which is an S or T. ( ) represents a tentatively identified amino acid.

All four of these tryptic peptides are found in the exons and putative cDNA sequence of meg-CSF.

EXAMPLE 5

Genomic Cloning of Urinary meg-CSF.

Probes consisting of pools of oligonucleotides or unique oligonucleotides are designed from the tryptic sequences above according to the method of R. Lathe, *J. Mol. Biol.*, 183(1):1–12 (1985). The following oligonucleotide probes are synthesized on an automated DNA synthesizer, with N representing any of the four nucleotides A, T, C, or G; R representing the nucleotides A or G; Y representing the nucleotides C or T; and H representing the nucleotides A, T, or C:

(1) TGYTTYGARTCNTTYGA
(2) TGYTTYGARAGYTTYGA
(3) GTNTGYACNGCNGARYT
(4) AARGCNCCNCCNCCN
(5) GCNAGYCARACNATHAA
(6) GCNTCNCARACNATHAA
(7) AARTAYGAYAARTGYTG
(8) GCNGARGTNCAYAAYCC
(9) AAGTATGACAAGTGCTGCCCTGATGAGTCCTTCTGTGCTGAGGTGCACAACCCC; and
(10) AAGTATGACAAGTGCTGCCCTGATGAGAGCTTCTGTGCGAGGTGCACAACCC Because the genetic code is degenerate (more than one codon can code for the same amino acid) a mixture of oligonucleotides are synthesized that contain all possible nucleotide sequences encoding the amino acid sequence of the selected tryptic fragment or portion thereof. It may be possible in some cases to reduce the number of oligonucleotides in the probe mixture based on codon usage because some codons are rarely used in eukaryotic genes, and because of the relative infrequency of the dinucleotide CpG in eukaryotic coding sequences [see J. J. Toole et al, *Nature*, 312:342–347 (1984)]. The regions of the amino acid sequences used for probe design are chosen by avoiding highly degenerate codons where possible. The oligonucleotides are synthesized on an automated DNA synthesizer and the probes are then radioactively labelled with polynucleotide kinase and $^{32}$P-ATP.

The degenerate oligonucleotide probes are then used to screen a human genomic library prepared from placenta [Stratagene Cloning Systems, La Jolla, Calif.] using established techniques [See K. Jacobs et al, *Nature*, 313:806–810 (1985)]. Recombinants from this library are plated and duplicate nitrocellulose and/or nylon replicas are made of the plates. Typically, the oligonucleotides are kinased with $^{32}$P gamma ATP and hybridized to the filters at 48° C. in 3M TMAC solution for 48–96 hours. The filters are then washed in 3M TMAC in 50 mM Tris at 50° C. for 1 hour followed by two washes at room temperature for 30 minutes each in 2×SSC [See K. Jacobs et al, *Nucleic Acids Res.*, 16:4637–4650 (1988)]. Duplicate positives are plaque purified.

An 18.3 kb genomic fragment (FIG. 3) was shown to hybridize to all four tryptic sequences. The first partial genomic subclone contained within the 18.3 kb insert to be isolated and sequenced was shown to contain one tryptic sequence (a) in a single exon (Exon II) and two partial tryptic sequences (b and d) which are contained in Exon II and overlap with adjacent coding sequence. Exon III was identified with a probe made from tryptic (c). Exon I was identified with a probe made to the 5' end of tryptic (b).

The predicted cDNA and predicted amino acid sequences of these combined partial genomic clones are reported in FIG. 2 above, which encodes a portion of the meg-CSF protein. While the peptide encoded by this partial sequence may produce an active meg-CSF fragment, the sequence lacks the amino terminal Met as well as any defined 3' border. To obtain the remainder of the meg-CSF genomic sequence, the full length genomic DNA sequence may be expressed in COS cells and a cDNA library prepared from COS cell RNA, and the cDNA sequence cloned from that source. Alternatively, the remainder of the sequence may be deduced by sequence comparison with a cross-hybridizing murine genomic meg-CSF sequence. The sequence may also be obtained from peripheral blood lymphocytes or placenta, two potential sources of the mRNA.

EXAMPLE 6

Expression of Recombinant Human meg-CSF

To produce meg-CSF or an active fragment thereof, the cDNA encoding it is transferred into an appropriate expression vector, of which numerous types are known in the art for human, insect, yeast, fungal and bacterial expression, by standard molecular biology techniques. One such vector for mammalian cells is pXM [Y. C. Yang et al, *Cell*, 47:3–10 (1986)]. This vector contains the SV40 origin of replication and enhancer, the adenovirus major late promoter, a cDNA copy of the adenovirus tripartite leader sequence, a small hybrid intervening sequence, an SV40 polyadenylation signal and the adenovirus VA I gene, in appropriate relationships to direct the high level expression of the desired cDNA in mammalian cells [See, e.g., Kaufman, *Proc. Natl. Acad. Sci. USA*, 82:689–693 (1985)]. The pXM vector is linearized with the endonuclease enzyme XhoI and subsequently ligated in equimolar amount separately to the cDNA encoding meg-CSF modified by addition of synthetic oligonucleotides [Collaborative Research, Lexington, Mass.] that generate Xho I complementary ends to generate constructs for expression of meg-CSF.

Another vector which may be employed to express meg-CSF in CHO cells is pEMC2B1. This vector may be derived from pMT2pc which has been deposited with the American Type Culture Collection (ATCC), Rockville, Md. (USA) under Accession Number ATCC 40348. The DNA is linearized by digestion of the plasmid with PstI. The DNA is then blunted using T$_4$ DNA polymerase. An oligonucleotide 5' TGCAGG-CGAGCCTGAA TTCCTCGA 3' is then ligated into the DNA, recreating the PstI site at the 5' end and adding an EcoRI site and XhoI site before the ATG of the DHFR cDNA. This plasmid is called pMT21. pMT21 is cut with EcoRI and XhoI which cleaves the plasmid at two adjacent cloning sites. An EMCV fragment of 508 base pairs was cut from pMT$_2$ECAT$_1$ [S. K. Jong et al, *J. Virol.*, 63:1651–1660 (1989)] with the restriction enzymes EcoRI and TaqαI. A pair of oligonucleotides 68 nucleotides in length were synthesized to duplicate the EMCV sequence up to the ATG. The ATG was changed to an ATT, and a C is added, creating a XhoI site at the 3' end. A TaqαI site is situated at the 5' end. The sequences of the oligonucleotides were:

5' CGAGGTTAAAAAACGTCTAGGCCCCCCGAACCACGGGGACGTGGTTTTCCTTT GAAAAACACGATTGC 3' and its complementary strand.

Ligation of the pMT21 EcoRI-to-XhoI fragment to the EMCV EcoRI-to-TaqαI fragment and to the TaqαI/XhoI oligonucleotides produced the vector pEMC2B1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells. The EMC2B1 vector is linearized with the endonuclease enzyme EcoRI and subsequently ligated in equimolar amount separately to the cDNA encoding meg-CSF that was previously modified by addition of synthetic oligonucleotides that generate EcoRI complementary ends to generate constructs for expression.

The desired vector containing meg-CSF is then introduced into appropriate host cells by conventional genetic engineering techniques. The transformed cells are cultured and the expressed meg-CSF is recovered and purified from the culture medium using standard techniques.

A. Mammalian Cell Expression

To obtain expression of the meg-CSF polypeptide in mammalian host cells, the pXM vector containing the meg-CSF DNA sequence is transfected onto COS cells. The conditioned medium from the transfected COS cells contains meg-CSF biological activity as measured in the murine assays. Similarly the pEMC2B1 construct containing the cDNA for meg-CSF is transfected into CHO cells.

The mammalian cell expression vectors described herein may be synthesized by techniques well known to those skilled in this art. One skilled in the art can also construct other mammalian expression vectors comparable to the pXM vector by, e.g., inserting the DNA sequence of the meg-CSF from the plasmid with appropriate enzymes and employing well-known recombinant genetic engineering techniques and other known vectors, such as pJL3 and pJL4 [Gough et al., *EMBO J.*, 4:645–653 (1985)] and pMT2 (starting with pMT2-VWF, ATCC #67122; see PCT application PCT/US87/00033).

Mammalian host cells other than COS cells may also be employed in meg-CSF expression. For example, preferably for stable integration of the vector DNA, and for subsequent amplification of the integrated vector DNA, both by conventional methods, CHO cells may be employed as a mammalian host cell of choice.

Once the vectors and host cells are selected and transformed, stable transformants are then screened for expression of the product by standard immunological, biological or enzymatic assays, such as those described below in Example 8. The presence of the DNA and mRNA encoding the meg-CSF polypeptides may be detected by standard procedures such as Southern and Northern blotting. Transient expression of the DNA encoding the polypeptides during the several days after introduction of the expression vector DNA into suitable host cells is measured without selection by activity or immunologic assay, e.g., the murine fibrin clot assay, of the proteins in the culture medium.

B. Bacterial Expression Systems

Similarly, one skilled in the art could manipulate the sequences encoding the meg-CSF polypeptide by eliminating any human regulatory sequences flanking the coding sequences and inserting bacterial regulatory sequences to create bacterial vectors for intracellular or extracellular expression of the meg-CSF polypeptide of the invention by bacterial cells. The DNA encoding the polypeptides may be further modified to contain different codons to optimize bacterial expression as is known in the art. Preferably the sequences encoding the mature meg-CSF are operatively linked in-frame to nucleotide sequences encoding a secretory leader polypeptide permitting bacterial expression, secretion and processing of the mature meg-CSF polypeptides, also by methods known in the art. The expression of meg-CSF in *E. coli* using such secretion systems is expected to result in the secretion of the active polypeptide. This approach has yielded active chimeric antibody fragments [See, e.g., Bitter et al, *Science*, 240:1041–1043 (1983)]. Alternatively, the meg-CSF may be expressed as a cytoplasmic protein in *E. coli*. In this case, the molecule would most likely have to be refolded after complete denaturation with guanidine hydrochloride, a process also known in the art. For procedures for isolation and refolding of intracellularly expressed proteins, see, for example, U.S. Pat. No. 4,512,922.

The compounds expressed through either route in bacterial host cells may then be recovered, purified, and/or characterized with respect to physicochemical, biochemical and/or clinical parameters, all by known methods.

C. Insect or Yeast Cell Expression

Similar manipulations can be performed for the construction of an insect vector for expression of meg-CSF polypeptides in insect cells [See, e.g., procedures described in published European patent application 155,476].

Similarly yeast vectors are constructed employing yeast regulatory sequences to express cDNA encoding the precursor, in yeast cells to yield secreted extracellular active meg-CSF. Alternatively the polypeptide may be expressed intracellularly in yeast, the polypeptide isolated and refolded to yield active meg-CSF. [See, e.g., procedures described in published PCT application WO 86/00639 and European patent application EP 123,289.]

EXAMPLE 7

Construction of CHO Cell Lines Expressing High Levels of meg-CSF

One method for producing high levels of the meg-CSF protein of the invention from mammalian cells involves the construction of cells containing multiple copies of the cDNA encoding the meg-CSF.

The cDNA is co-transfected with an amplifiable marker, e.g., the DHFR gene for which cells containing increasing concentrations of methotrexate (MTX) according to the procedures of Kaufman and Sharp, *J. Mol. Biol.*, (1982) supra. This approach can be employed with a number of different cell types. Alternatively, the meg-CSF cDNA and drug resistance selection gene (e.g., DHFR) may be introduced into the same vector. A preferred vector for this approach is pEMC2B1.

For example, the pXM vector containing the meg-CSF gene in operative association with other plasmid sequences enabling expression thereof is introduced into DHFR-deficient CHO cells, DUKX-BII, along with a DHFR expression plasmid such as pAdD26SVpA3 [Kaufman, *Proc. Natl. Acad. Sci. USA*, 82.:689–693 (1985)] by calcium phosphate coprecipitation and transfection.

Alternatively, the pEMC2B1 vector containing the meg-CSF gene in operative association with other plasmid sequences enabling expression thereof is introduced into DHFR-deficient CHO cells, DUKX-BII, by protoplast fusion and transfection. The meg-CSF gene and DHFR marker gene are both efficiently expressed when meg-CSF is introduced into pEMC2B1. The meg-CSF gene may be introduced into pMT2 as previously mentioned and the resultant vector used in place of pXM/meg-CSF and pAdA26SV (A)3.

DHFR expressing transformants are selected for growth in alpha media with dialyzed fetal calf serum. Transformants are checked for expression of meg-CSF by bioassay, immunoassay or RNA blotting and positive pools are subsequently selected for amplification by growth in increasing concentrations of MTX (sequential steps in 0.02, 0.2, 1.0 and 5 uM MTX) as described in Kaufman et al.,*Mol. Cell Biol.*, 5:1750 (1983). The amplified lines are cloned, and meg-CSF protein expression is monitored by the fibrin clot assay. meg-CSF expression is expected to increase with increasing levels of MTX resistance.

In any of the expression systems described above, the resulting cell lines can be further amplified by appropriate drug selection, resulting cell lines recloned and the level of expression assessed using the murine fibrin clot assay described above.

The meg-CSF expressing CHO cell lines can be adapted to growth in serum-free medium. Homogeneous meg-CSF can be isolated from conditioned medium from the cell line using methods familiar in the art, including techniques such as lectin-affinity chromatography, reverse phase HPLC, FPLC and the like.

EXAMPLE 8

Bioloqical Activities of Human meg-CSF

The following assays were performed using the purified meg-CSF described in Example 1. The recombinant version of the molecule is expected to exhibit meg-CSF biological properties in these same assays or other assays.

A. Murine Fibrin Clot Assay

The meg-CSF obtained from Step 7 of the purification techniques of Example 1 was tested for activity in the megakaryocyte colony formation assay performed substantially as described in S. Kuriya et al, *Exp. Hematol.*, 15:896–901 (1987). A fibrin clot was formed containing $2.5 \times 10^5$ mouse bone marrow cells in a 96-well plate. The diluted sample was layered around the clot and incubated for 6 days. Thereafter, cells were fixed and megakaryocytes were stained for acetylcholinesterase, a specific marker for murine megakaryocytes. A colony was defined as three or more megakaryocytes per unit area. Two types of megakaryocyte colonies were routinely observed: pure megakaryocyte colonies containing no additional cell types, and mixed megakaryocyte colonies containing additional non-megakaryocyte cell types.

The following control samples were included in every assay. A positive control was WEHI conditioned medium (murine Il14 3), which produced between 7–25 (average 12) megakaryocyte colonies per clot, approximately 50% pure and 50% mixed megakaryocyte colonies. Another positive control was serum taken from lethally irradiated dogs at the nadir of the platelet count [see Mazur et al, *Exp. Hematol.*, 13:1164–1172 (1985)], which produced between 6–22 (average 15) megakaryocyte colonies per clot, of which approximately 70% were pure and 30% were mixed megakaryocyte colonies. The negative control was Iscoves Medium, which produced 2–4 megakaryocyte colonies per clot.

In the assay, the meg-CSF has a specific activity of greater than approximately $5 \times 10^7$ dilution units/mg of protein. A unit of activity is defined as described in Example 3.

The major meg-CSF obtained from bone marrow transplant urine eluted from the S-Toyopearl cation exchange column chromatography step in the purification of Example 1 has been analyzed in this assay alone, together, and in combination with other cytokines. In the fibrin clot assay, it produced between 6–16 (average 13) megakaryocyte colonies, with 50–70% pure megakaryocyte colonies.

In each assay the samples were tested in duplicate and in three dilutions.

B. Human Plasma Clot meg-CSF Assay

The meg-CSF of this invention was also tested on an assay for human activity, the plasma clot meg-CSF assay described in E. Mazur et al, *Blood*, 57:277–286 (1981) with modifications. Non-adherent peripheral blood cells were isolated from Leukopacs and frozen in aliquots. The test sample was mixed with platelet-poor human AB plasma and $1.25 \times 10^5$ cells in 24-well plates and allowed to clot by the addition of calcium. After a 12 day incubation, megakaryocytes were identified using a monoclonal antibody directed against platelet glycoproteins IIb/IIIa and a horseradish peroxidase/anti-peroxidase chromogenic detection system.

Recombinant human IL-3 [Genetics Institute, Inc.] was used as a positive control, producing 12-30 megakaryocyte colonies per clot with approximately 60% pure and 40% mixed megakaryocyte colonies. As in the murine assay, the aplastic dog serum was also used as a positive control, which produced between 5-10 megakaryocyte colonies per clot, of which approximately 50% were pure megakaryocyte colonies contained less than 10 cells, and 50% were mixed megakaryocyte colonies containing more than 40 megakaryocytes. The negative control was Alpha Medium, which produced 0-1 megakaryocyte colonies per clot.

The meg-CSF product from Step 8 of the above-described purification scheme may be active in this assay.

C. Murine meg-CSF Assay

An assay was performed on the meg-CSF from Step 7 of the purification according to P. J. Quensenberry et al, *Blood*, 65(1):214-217 (1985). In the assay, the meg-CSF stimulates the growth of acetylcholinesterase positive megakaryocyte colonies containing on average between 4-15 cells per colony. The sizes of the megakaryocytes are variable ranging from small immature cells to morphologically large mature cells.

D. Other assays

Several additional megakaryocyte assays using murine bone marrow cells were employed including the liquid acetylcholinesterase induction assay of Ishibashi et al, *Blood*, 69:1737-1741 (1987) and the liquid serotonin uptake assay of Vanucchi et al, *exp. Hematol.*, 16:916-921 (1988).

Fractions were also routinely assayed in several factor dependent cell lines to screen for the presence of growth factors which alone or in combination might stimulate colony formation. The cell lines used were the human erythroleukemic cell line TF-1, the human megakaryoblastic cell line MO-7, the murine Il-6-dependent cell line Tl165, and the murine IL-3-dependent cell line DA-1a.

The foregoing descriptions detail presently preferred embodiments of the invention. Numerous modifications and variations in practice of this invention are expected to occur to those skilled in the art. Such modifications and variations are encompassed within the following claims.

What is claimed is:

1. A human megakaryocyte colony stimulating factor protein, substantially free from association with other proteinaceous material, said protein being characterized by possessing
   (a) the ability to stimulate growth and development of colonies consisting of megakaryocyte cells;
   (b) an apparent molecular weight of about 28-38 kd as determined by 12% sodium dodecyl sulfate polyacrylamide gel electrophoresis under non-reducing conditions;
   (c) an apparent molecular weight of about 20-27 kd as determined by 12% sodium dodecyl sulfate polyacrylamide gel electrophoresis under reducing conditions; and
   (d) a partial amino acid sequence selected from the group consisting of:
      (i) Ser Arg Cys Phe Glu Ser Phe Glu Arg;
      (ii) Arg Val Cys Thr Ala Glu Leu Ser Cys Lys Gly;
      (iii) Lys Ala Pro Pro (X) Gly Ala Ser Gln Thr Ile Lys; and
      (iv) Lys Tyr Asp Lys Cys Cys Pro Asp Tyr Glu Ser Phe Cys Ala Glu Val His Asn Pro, wherein (X)=Ser or Thr.

2. The protein of claim 1 further characterized by possessing a specific activity of between approximately $5 \times 10^7$ and $5 \times 10^8$ dilution units/mg protein in a megakaryocyte colony formation assay.

3. The protein of claim 2 wherein said specific activity is $2 \times 10^8$ dilution units/mg protein.

4. The protein of claim 1, produced by subjecting urine from human bone marrow patients to purification comprising the steps of:
   (a) concentrating said urine;
   (b) subjecting the resulting retentate to anion exchange column chromatography;
   (c) subjecting the flow-through from step (b) to cation exchange column chromatography;
   (d) eluting the material from step (c) through lectin affinity column chromatography;
   (e) subjecting the eluate from step (d) to cation exchange fine performance liquid chromatography;
   (f) diluting the eluate from step (e) with two parts TFA and subjecting it to reverse phase high pressure liquid chromatography in a solvent of acetonitrile and trifluoroacetic acid;
   (g) diluting the eluate from step (f) with two parts pyridine and acetic acid and subjecting it to a second reverse phase high pressure liquid chromatography in a solvent of n-propanol, pyridine and acetic acid.

5. The protein of claim 4, additionally comprising the step of subjecting the eluate from step (g) to a third reverse phase high pressure liquid chromatography in a solvent of acetonitrile in heptofluorobutyric acid.

6. A pharmaceutical composition comprising a therapeutically effective amount of the protein of claim 1 in a pharmaceutically effective vehicle.

7. A pharmaceutical composition comprising a therapeutically effective amount of the protein of claim 4 in a pharmaceutically effective vehicle.

* * * * *

UNITED STATES PATENT AND TRADEMARK OFFICE
CERTIFICATE OF CORRECTION

PATENT NO. : 5,326,558
DATED : July 5, 1994
INVENTOR(S) : K. Turner, et al

It is certified that error appears in the above-indentified patent and that said Letters Patent is hereby corrected as shown below:

At column 5, line 61 (page 14, line 5), replace "()" with --( )--.

At column 20, line 3 (page 57, line 14), replace "Bioloqical" with --Biological--.

At column 20, line 30 (page 58, line 15), replace "(murine Il143)" with --(murine Il-3)--.

At column 22, line 14, replace "(iii) Lys Ala Pro Pro (X) Gly Ala Ser Gln Thr Ile Lys;" with --Lys Ala Pro Pro Pro (X) Gly Ala Ser Gln Thr Ile Lys;".

DRAWINGS:

IN FIGURE 3:

Please replace all of the occurrences of the word "Xpa" with --Xba--.

Signed and Sealed this

Sixth Day of June, 1995

*Attest:*

BRUCE LEHMAN

*Attesting Officer*      *Commissioner of Patents and Trademarks*